United States Patent [19]

Lai et al.

[11] Patent Number: 4,762,872

[45] Date of Patent: Aug. 9, 1988

[54] OLIGOMERIC LIGHT STABILIZERS WITH SUBSTITUTED PIPERIDINE ENDS

[75] Inventors: John T. Lai, Broadview Heights; Pyong Nae-Son, Akron, both of Ohio

[73] Assignee: The B. F. Goodrich Company, Akron, Ohio

[21] Appl. No.: 74,831

[22] Filed: Jul. 17, 1987

Related U.S. Application Data

[63] Continuation-in-part of Ser. No. 793,823, Nov. 1, 1985, abandoned.

[51] Int. Cl.$^4$ .................. C08K 5/34; C07D 211/32
[52] U.S. Cl. .................. 524/100; 524/103; 528/229; 544/357; 544/364; 546/16; 546/187; 546/190
[58] Field of Search .............. 524/100, 103; 544/357, 544/364; 546/16, 187, 190; 528/229

[56] References Cited

U.S. PATENT DOCUMENTS

| | | | |
|---|---|---|---|
| 3,247,200 | 4/1966 | Ugi et al. | 546/224 |
| 3,840,494 | 10/1974 | Murayama et al. | 546/217 |
| 3,960,984 | 6/1976 | Kohan | 525/400 |
| 4,058,523 | 11/1977 | Mori et al. | 546/234 |
| 4,069,196 | 1/1978 | Ramey et al. | 546/222 |
| 4,069,199 | 1/1978 | Ramey et al. | 546/221 |
| 4,191,683 | 3/1980 | Brunetti et al. | 524/103 |
| 4,293,468 | 10/1981 | Rody | 546/216 |
| 4,310,429 | 1/1982 | Lai | 544/106 |
| 4,331,585 | 5/1982 | Valdiserri et al. | 524/103 |
| 4,440,887 | 4/1984 | Hinsken et al. | 524/103 |
| 4,466,915 | 8/1984 | Lai | 546/223 |
| 4,473,694 | 9/1984 | Lai | 546/190 |
| 4,500,662 | 2/1985 | Lai | 524/100 |
| 4,501,837 | 2/1985 | Cantature | 524/103 |
| 4,525,503 | 6/1985 | Cantature | 524/103 |

FOREIGN PATENT DOCUMENTS 1516779 11/1976 United Kingdom.
1496635 12/1977 United Kingdom.

*Primary Examiner*—John Kight
*Assistant Examiner*—Kriellion Morgan
*Attorney, Agent, or Firm*—Alfred D. Lobo; Alan A. Csontos

[57] ABSTRACT

A poly($\alpha$-aminoacetamide) ("poly(AAMID)" for brevity) main chain having terminal polysubstituted piperidinyl chain ends are novel compounds which have highly desirable UV-light stabilizing (UV-S) activity coupled with unexpectedly good thermal stability. These compounds, referred to as "piperidinyl-chain ended poly(AAMID)s", are oligomers which contain from 2 to about 18 AAMID repeating units, for use in polymer recipes to formulate a stabilized polymeric composition comprising a UV-light-degradable organic polymer containing an effective amount of the poly(AAMID) sufficient to stabilize the polymer. A poly(AAMID) is especially effective in a polyolefin in which there is from about 0.1 percent by weight (% by wt), to about 5% by wt of the oligomer, and is also effective in a wide variety of pastel colored and/or transparent commercially significant polymers.

10 Claims, No Drawings

OLIGOMERIC LIGHT STABILIZERS WITH SUBSTITUTED PIPERIDINE ENDS

CROSS REFERENCE TO RELATED APPLICATION:

This is a continuation-in-part application of Ser. No. 793,823 filed Nov. 1, 1985, now abandoned.

BACKGROUND OF THE INVENTION

This invention is related to oligomeric light stabilizers containing an alpha-aminoacetamide ("AAMID") repeating unit and polysubstituted piperidine chain ends. The term "polysubstituted" refers specifically to a piperidine ring in which at least the N-adjacent carbon atoms in the piperidine ring are each dialkylsubstituted, or one of the 2 or 6 C atoms is shared by a spiro cycloalkylene substituent, and the other is dialkyl-substituted. Polysubstituted piperidine compounds belong to a class of compounds referred to as hindered amines which are known to be useful as ultraviolet ("UV") light stabilizers in organic materials, whether natural or synthetic, which are to be protected against degradation by UV light.

More specifically the compounds of this invention include hindered piperidine moieties, and hindered piperidine moieties are an essential constituent of a large number of UV stabilizers and antioxidants. For example, U.S. Pat. No. 3,840,494 discloses 4-piperidinol derivatives, and Nos. 3,904,581 and 3,968,078 disclose piperidine derivatives as being good stabilizers. U.S. Pat. No. 4,293,468 discloses 4-oxo-piperidines and No. 4,293,468 discloses piperidine phosphite stabilizers; Nos. 4,069,196 and 4,069,199 disclose polypiperidines as do Great Britain Nos. 1,496,635 and 1,516,779.

Though many polysubstituted piperidines have a significant level of UV-stabilization ("UV-S") activity, each has one or more serious drawbacks which makes the one less desirable from a practical and utilitarian point of view, than another having a less serious drawback. This reality dictates the unending search, even in the narrow field of piperidine-based stabilizers, for compounds with better UV-S activity, and results in discarding numerous stabilizers which do not have commercially significant activity.

The effectiveness of the polymer of this invention is deemed to be derived as much from the poly(AAMID) body of the compounds as from the hindered piperidine chain ends. The preparation of AAMID compounds has been disclosed in U.S. Pat. No. 4,310,429 and these compounds were used primarily as antioxidants, though they exhibit other desirable stabilizing properties, and are particularly for use in synthetic ester lubricants generally known as "functional fluids".

Amino-acid amides are disclosed in earlier U.S. Pat. Nos. 2,153,707 and 3,247,200; and 3,960,984 which is incorporated by reference thereto as if fully set forth herein, discloses amide oligomers as heat stabilizers for oxymethylene polymers. Still other amides useful as antioxidants are disclosed in U.S. Pat. No. 3,665,031; and more recent U.S. Pat. Nos. 4,058,523; 4,139,605; 4,239,747; 4,250,794; and 4,336,116 disclose other amides for a variety of purposes.

The key to the preparation of the compounds of this invention is the use of the specified substituents on the pyridine and the specified diamine in a "ketoform reaction" carried out without a phase transfer catalyst, as disclosed in U.S. Pat. No. 4,466,915 which is incorporated by reference thereto as if fully set forth herein. Quite unexpectedly, the reaction results in the formation of a polymer having the AAMID repeating unit, and this polymer has highly desirable UV-S properties.

SUMMARY OF THE INVENTION

It has been discovered that a poly(alpha-aminoacetamide) chain ("poly(AAMID)" for brevity) having terminal polysubstituted piperidine moieties provides a novel oligomer which has highly desirable UV-light stabilizing (UV-S) activity coupled with unexpectedly good thermal stability when used in organic polymers.

It is therefore a general object of this invention to provide a class of compounds comprising a poly(AAMID) with terminal piperidine moieties in which the ring N atom is hindered by substituents on the N-adjacent C atoms.

It is also a general object of this invention to provide a stabilized oligomeric composition comprising a light-degradable organic polymer, particularly a synthetic resinous material, containing an effective amount of a poly(AAMID) sufficient to stabilize the polymer.

It is a specific object of this invention to provide a stabilized oligomeric composition comprising an oligomer of a mono-1-olefin having incorporated therein less than 1 percent by weight (% by wt) of a poly(AAMID).

It has also been discovered that a poly(AAMID) may be prepared in a single step process by a reaction with (i) a 2,6-polysubstituted pyridine having an alkylamino- or hydroxyalkylamino-, or N-alkylaminoalkylamino- substituent on the 4-carbon atom, (ii) a diamine, (iii) a ketone and (iv) chloroform or bromoform in the presence of a strong base.

It is therefore a general object of this invention to provide a convenient and effective single step process utilizing a ketoform reaction to produce a poly(AAMID) oligomer having polysubstituted piperidine chain ends each having a hindered $N^1$ atom.

DETAILED DESCRIPTION OF PREFERRED EMBODIMENTS

The structure of the poly(AAMID) compound is represented as follows:

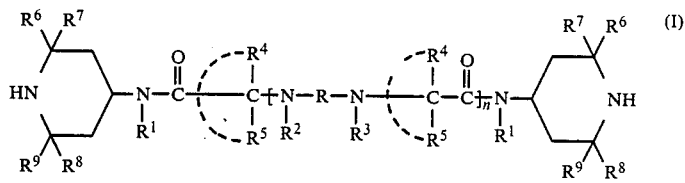

wherein, R represents $C_2$–$C_{18}$ alkylene, $C_6$–$C_{18}$ aryl, $C_7$–$C_{18}$ alkaryl or aralkyl, methylene-bis-$C_6$–$C_{18}$ aryl, piperazinediyl or aryl substituted with Cl or Br, $C_1$–$C_6$ alkoxy, monocyano, or mononitro;

$R^1$, $R^4$ and $R^5$ represent a substituent selected from the group consisting of $C_1$–$C_{20}$ alkyl, hydroxyalkyl, and N-alkylaminoalkyl, with $R^4$ and $R^5$ in combination being cyclizable to form a 5- to 8-membered alicyclic ring, typically cyclohexyl or cycloheptyl; and, in addition, only $R^1$ may be H;

$R^2$ and $R^3$ represent H or $C_1$–$C_{18}$ alkyl;

$R^6$, $R^7$, $R^8$, and $R^9$ independently represent $C_1$–$C_{24}$ alkyl, and $C_4$–$C_7$ polymethylene which are cyclizable forming a spiro cycloalkylene substituent with the C atom of the piperidine ring; and, n is an integer in the range from 2 to about 18.

Most preferably R represents one or more of the following, derived from aromatic or alicyclic diamines, it being understood that mixtures may be used, if desired:

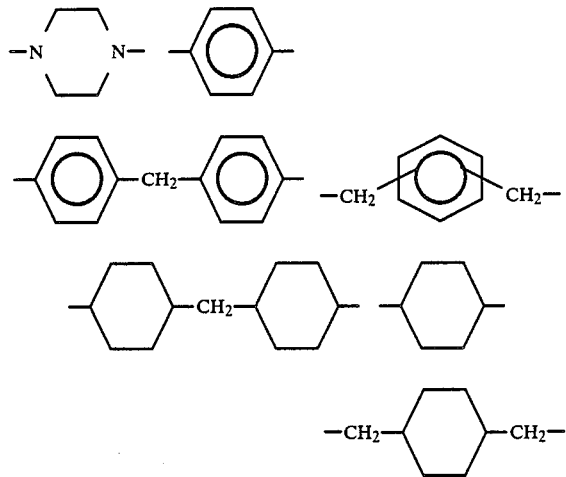

When mixtures are used, the oligomer will be random, containing amide repeating units occurring randomly though the oligomer may also include short polyamide blocks derived from each diamine.

The poly(AAMID)s are generally solids, and soluble or partially soluble in acetone, diethyl ether, dioxane, tetrahydrofuran, carbon tetrachloride, chloroform, lower primary alcohols having from 1 to about 5 C atoms such as methanol, ethanol and propanol, aromatic hydrocarbons such as benzene and toluene, but much less soluble in aliphatic hydrocarbons such as hexane. Poly(AAMID)s are generally insoluble in water. They are white when pure.

The amount of stabilizer employed will vary with the particular material to be stabilized and also the substituents used. Generally however, for effective UV stabilization of organic materials, an amount of the poly(AAMID) used is in the range from about 0.01% by wt to about 10% by wt, based on the wt of organic material. In typical stabilized polymers, and particularly in synthetic resinous materials, the amount of poly(AAMID) used is in the range from about 0.01 to about 5% by wt.

Compositions of this inventions are the stabilized materials which combat the deleterious effects of uv light, thermal or oxidative degradation such as are usually evidenced by discoloration and/or embrittlement. These compositions generally benefit from the inclusion of additional secondary stabilizers to achieve even greater stability against a combination of actinic light, heat and oxygen. Therefore, in conjunction with the stabilizers of this invention, compositions may include secondary stabilizers which may be present in the range from about 0.01 to about 10 phr, and preferably from about 0.1 to about 5 phr of the organic continuous phase. Several types of known secondary stabilizers may be used, such as those disclosed in U.S. Pat. Nos. 3,325,448; 3,769,259; 3,920,659; 3,962,255; 3,966,711; 3,971,757; inter alia.

Organic materials which may be stabilized against uv light, thermal and oxidative degradation, include copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, polycarbonates, varnish, phenol-formaldehyde resins, polyepoxides, polyesters, and polyolefin homo- and copolymers such as polyethylene, polypropylene, ethylene-propylene polymers, ethylene-propylenediene polymers, ethylene vinyl acetate polymers and the like. The poly(AAMID)s can also be used to stabilize mixtures and blends of oligomeric materials such as ABS resin blends, PVC and polymethacrylate blends, and blends of homopolymers and copolymers such as blends of polypropylene in EPDM polymers.

Most particularly, the poly(AAMID)s are especially useful as uv-light stabilizers for synthetic resinous materials used in the form of fibers, or in thermoformed shapes which are at least partially permeable to visible light, and particularly for those which are transparent thereto, such as polyvinylaromatics and polyolefins.

Many known compounding ingredients may be used along with the poly(AAMID)s in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin and the like.

Particularly desirable secondary stabilizers are one or more antioxidants used in the range from about 0.01 phr to about 20 phr, preferably from about 0.1 to about 5 phr of the material to be stabilized. Of the types of antioxidants used, are phosphite, phosphate, sulfide and phenolic antioxidants, the last being preferred. Most preferred are the hindered phenol AOs specified hereinabove, though others are also useful such as 2,6-di-t-butyl-paracresol; 2,2'-methylene-bis(6-t-butyl-phenol); 2,2'-thiobis(4-methyl-6-t-butylphenol); 2,2'-methylene-bis(6-t-butyl-4-ethyl-phenol); 4,4'-butylidene-bis(6-t-butyl-m-cresol); 2-(4-hydroxy3,5-di-t-butylanilino)-4,6-bis(octylthio)-1,3,5-triazine; benzenepropanoic acid, 3,5-bis(1,1-dimethylethyl)-4-hydroxy-,(2,4,6-trioxo-1,3,5-triazine-1,3,5(2H,4H,6H)-triyl)tri-2,1-ethanediyl ester (Goodrite ®3125); tetrakis[methylene 3-(3',5'-di-t-butyl4'-hydroxyphenyl)propionate]methane; and particularly commercially available antioxidants such as Irganox 1010, 1035, 1076 and 1093. Other ingredients such as pigments, tackifiers, flame retardants, fungicides, and the like may also be added.

The poly(AAMID)s, and other compounding ingredients if used, can be admixed with the material to be stabilized using known mixing techniques can equipment such as internal mixing kettles, a Banbury mixer, a Henschel mixer, a two-roll mill, an extruder mixer, or other standard equipment, to yield a composition which may be extruded, pressed, blowmolded or the like into film, fiber or shaped articles. Usual mixing times and temperatures can be employed which may be determined with a little trial and error for any particular composition. The objective is to obtain intimate and uniform mixing of the components. A favorable mixing procedure to use when adding a poly(AAMID) to an organic material is either to dissolve or suspend the poly(AAMID) in a liquid such as methylene chloride before adding it, or to add the poly(AAMID) directly to the oligomeric material whether the poly(AAMID) is in the form of a powder or oil, or to extruder-mix the poly(AAMID) and material prior to forming the product.

The UV-stability of a stabilized composition can be evaluated by exposing a prepared sample of the composition to Xenon or carbon arc light in a Weather-0-Meter (ASTM D2569-79) operating at a temperature of about 145° E. (63° C.) at about 50% relative humidity. Degradation of the sample is monitored by periodically measuring the tensile strength after exposure, and the hydroperoxide absorption band at 3460 cm$^{-1}$ or carbonyl absorption band at 1720 cm$^{-1}$ using an IR spectrophotometer. The rapid formation of carbonyl indicates failure of the sample. The test procedure is well known, and is published in the text *Photodegradation, Photooxidation and Photostabilization of Polymers* by Ranby and Rabek, John Wiley & Sons, N.Y., N.Y. (1975), at pg 129 et seq., and is disclosed in U.S. Pat. No. 3,909,493. Failure of the sample is also checked by visual signs of cracking when the sample is bent 180°. Degradation of fibers is checked by suspending lengths of fiber spaced about 0.125″ apart on a stainless steel holder and testing three of them periodically until it is found that they suffer a 50% loss of initial tensile strength (ASTM D2343-67).

Samples of the compositions are also checked for oxidative and thermal stability by measuring the time to discoloration and/or embrittlement of the sample after aging in an air circulating oven at 125° C. (ASTM D1204-78), and other standard tests. These tests include tests for resistance to water extraction, perchloroethylene extraction, and "gas fade" as will be explained in greater detail hereinafter.

Preparation of P(AAMID)

In a typical preparation, a diamine which is to help generate the repeating unit of the polymer, chloroform, a ketone and a polysubstituted piperidine having an amino substituent at the 4-position are mixed in a cooled flask and aqueous concentrated NaOH slowly dripped into the flask while stirring and keeping the temperature below 5° C.

It is hypothesized that the diamine attacks the oxirane intermediate formed from chloroform and the ketone, generating an intermediate having the structure

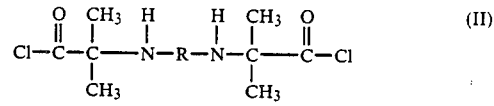

Subsequently, an amine group from an additional diamine molecule can attack either one of the carbonyl carbon atoms of (II), or the carbon atom of the precursor oxirane ring to which two methyl groups are attached. If the carbonyl atom is attacked by the amine attached to the piperidyl ring, there is no propagation of the repeating unit. It is only because the alpha-carbon atom is attacked, that the acyl group is maintained at the end of the extended chain. The repetitious occurrence of this attack on each side of the molecule (II) generates the oligomer until finally a free amine group from the polysubstituted piperidine attacks the carbonyly carbon atom and terminates the chain.

EXAMPLE 1

1.13 g (0.0059 mol) methylenebis(4-aminobenzene); 1.87 g (0.0157 mol) chloroform; 6.83 g (0.1176 mol) acetone; and, 3.33 g (0.0196 mol) 4-methylamino-2,2,6,6-tetramethylpiperidine are mixed in a 50 ml reaction flask equipped with a condenser, thermometer, mechanical stirrer and placed in a cooling bath cooled to about 0° C. 2.35 g of 50% aqueous NaOH was then added in portions, keeping the temperature below 10° C. by cooling to negate the effect of the exothermic reaction which was allowed to go to completion overnight. 20 ml acetone was added and the solid mass was stirred and filtered to obtain a filtrate (F), and to recover a white solid (S1) which was rinsed thoroughly with acetone, then with water, and filtered.

The filtrate was concentrated and vacuum dried, then stirred with hexanes and filtered to yield a white powder (S2). The solids S1 and S2 were found to have the same structure which was confirmed by IR, nmr and GC analysis to be as follows:

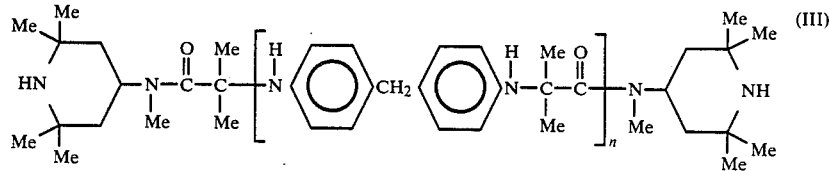

The m p of the solid is 171°–196° C. from 2 to 5 in this example, but under different reaction conditions can be from about 2–10.

EXAMPLE 2

1.98 g (0.01 mol) methylenebis(4-aminobenzene); 3.58 g (0.03 mol) chloroform; 14.42 g (0.20 mol) 2-butanone; and, 4.0 g (0.1 mol) 4-methylamino-2,2,6,6-tetramethylpiperidine are reacted in a manner analogous to that described in Example 1 hereinabove and the product worked up and recovered. The structure of the compound obtained is represented as follows:

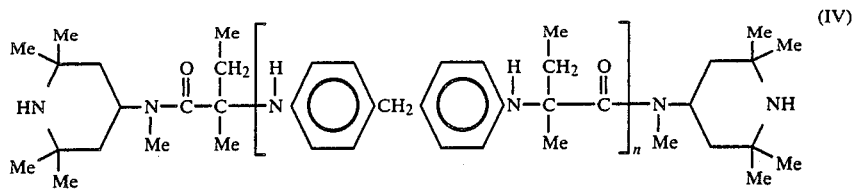

wherein n is in the range from 2 to about 5.

EXAMPLE 3

1.92 g (0.01 mol) methylenebis(4-aminobenzene); 3.34 g (0.028 mol) chloroform: 19.64 g (0.20 mol) cyclohexanone; and, 5.1 g (0.103 mol) 4-methylamino-2,2,6,6-tetramethylpiperidine are reacted in a manner analogous to that described in Example 1 hereinabove and the product worked up and recovered. The structure of the compound obtained is represented as follows:

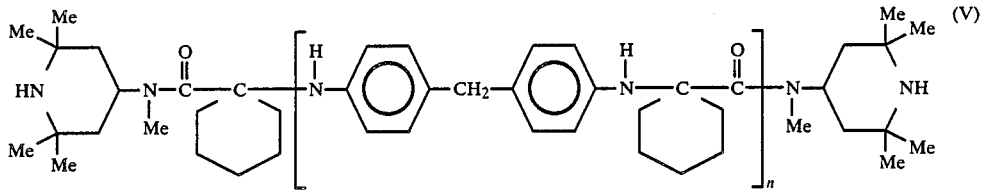

Recrystallization from heptane/toluene yielded a white powder for which the above structure was confirmed by analysis.

The following Table I sets forth data obtained in tests conducted with 2 mil thickness samples of polypropylene. The blank and each sample includes 0.05 phr of Goodrite ®3125 antioxidant, and the amount of stabilizer used in each sample is 0.1 phr. Oven aging is done at 125° C. in the standard test procedure, and the Weather-O-Meter tests give the number of hours after which a sample loses 50% of its original tensile strength. Chimassorb 944 is a commercially available polytriazine having piperidine substituents disclosed in U.S. Pat. No. 4,086,204.

TABLE I

| Stabilizer | Oven aging (days) | Xenon Weather-O-Meter (hr) Extraction with water | |
|---|---|---|---|
| | | Before | After |
| Blank | | | |
| Chimassorb 944 | 25 | 1720 | 1040 |
| III of Ex. | 18 | 1400 | 1200 |

Table II herebelow sets forth data obtained in oven aging and photostabilization tests conducted with yarn made of Profax 6301 polypropylene which consists of 40 filaments (approx 10 denier) for a total of 400-500 denier per yarn. Each piece of yarn (or 'fiber') including the blank, contained 0.1 phr of compound III made as described in Ex 1, and 0.1 phr Ca stearate.

Oven aging is done at 125° C. in a convection oven in a conventional manner except that samples are rotated manaually, daily. In this oven aging test, loops of yarn are suspended in an oven which substantially meets the requirements of ASTM D3012-79. A loop is removed from the oven every couple of days and tested for tensile strength. When the tensile is one-half (1/2) the original tensile, the sample is deemed to have failed.

Photostabilization is measured by Xenon Weather-O-Meter tests conducted with samples each of which consists of 30 or 40 slightly spaced-apart turns of filament on a stainless steel holder. A 2″ long piece of fiber (in triplicate) is removed every 300 hr and tested for tensile. When the tensile is ½ the original tensile, the sample is deemed to have failed.

TABLE II

| Stabilizer | Xenon W'er-O-Meter (hr) | Oven Aging (days) |
|---|---|---|
| III of Ex. 1 | 720 | 14 |
| Chimassorb 944 | 850 | 3 |

The most preferred utility for the compounds of this invention is in film, fiber and other shaped articles of the commercially important resins, many of which are pigmented or dyed with conventional relatively light colors, particularly pastel shades. Many of the compounds of this invention do not interfere with the color imparted by the pigment or dye, yet provide the desired stabilization, which is a highly merchantable trait.

The poly(AAMID)s of this invention are conveniently synthesized as oligomers having from 2 to about 10 repeating units and a number average mol wt in the range from about 1500 to about 20,000. In this mol wt range they are relatively non-volatile, resistant to extraction with common solvents, and compatible with conventional compounding ingredients such as processing oils, plasticizers, lubricants, fillers, reinforcing agents, rust inhibitors and the like, particularly those used with shaped polyolefin products, such as those made from polyethylene, polyvinyl chloride and polypropylene as illustrated.

What will particularly be appreciated by those skilled in the art, is the elegance and ease with which a poly(AAMID) oligomer may now be synthesized—which is the key to providing an affordable commercial product. For commercial production, the synthesis of the oligomer proceeds in a one-step reaction carried out in a single reaction vessel by simply mixing the reactants under the appropriate conditions.

The process is typically carried out by reacting (i) a primary diamine having any R group intermediate the primary amine groups, (ii) a monoketone, and (iii) a 4-alkylamino polysubstituted piperazine in the presence of a base and sufficient haloform so as to result in the formation of the oligomer having the desired repeating unit. The monoketone is preferably present an amount from about 2 to about 25 times greater than the molar amount required to react with the diamine. During the reaction, the temperature is maintained below that which will degrade the diamine used by using a reactor with a cooling jacket, and making sure that the base, preferably in the form of aqueous alkali metal hydroxide, is dripped in so as to maintain a suitable temperature. Recovering the oligomer is done as described in the examples, it being recognized that oligomers with different substituents and having different molecular weights may require some modifications of the recovery steps such as those skilled in the art would expect to make to obtain efficient recovery.

EXAMPLE 3

0.86 g (0.01 mol) piperazine; 3.58 g (0.03 mol) chloroform; 11.2 g (0.20) mol acetone; and, 0.38 g (0.01 mol) 4-amino-2,2,6,6-tetramethylpiperidine are reacted in a manner analogous to that described in Example 1 hereinabove and the product worked up and recovered. The structure of the compound obtained is represented as follows:

wherein n is in the range from 2 to about 5.

As seen from the foregoing example, piperazine is a cyclic diamine which is a secondary amine yet is an effective component of the repeating unit. The residue of an aromatic amine is introduced by reaction with an aromatic amine having primary amine groups as in example 1, where 4,4'-methylene-bis-aniline is used; this compound may be conveniently substituted with a mononitro, monocyano, lower $C_1$-$C_6$ alkoxy, or halogen substituent, as may be a xylidene residue. In an analogous manner, 4,4'-bis-cyclohexylamine with desired substituents may also be used to provide a cycloaliphatic component of the repeating unit.

In a typical preparation, the poly(AAMID) oligomer is formed with a range of repeating units, and some of the compounds formed may have a single AAMID unit. Where only oligomers having repeating units in a particular range are desired, it may be necessary to make the separation in an additional step.

From the foregoing it will be evident that the choice of substituents on the piperidyl chain ends in combination with those in the AAMID repeating unit will determine the performance characteristics of particular stabilizers. It is particularly noteworthy that the substituents $R^4$ and $R^5$ are derived from the ketone residual groups on either side of the carbonyl group, and these substituents may be cyclized so as to form a ring containing from 5 to about 8 carbon atoms, as for example, when cyclohexanone is used.

We claim:

1. A poly(α-aminoacetamide) ("poly(AAMID)") oligomer represented by the following structure:

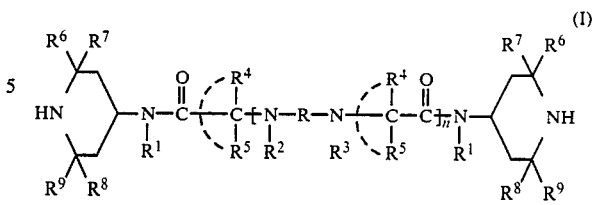

wherein, R represents $C_2$-$C_{18}$ alkylene, $C_6$-$C_{18}$ aryl, $C_7$-$C_{18}$ alkaryl or aralkyl, methylene-bis-$C_6$-$C_{18}$ aryl, piperazinediyl or aryl substituted with Cl or Br, $C_1$-$C_6$ alkoxy, monocyano, or mononitro;

$R^1$, $R^4$ and $R^5$ represent a substituent selected from the group consisting of $C_1$-$C_{20}$ alkyl, hydroxyalkyl, and N-alkylaminoalkyl, with $R^4$ and $R^5$ in combination being cyclizable to form a 5- to 8-membered alicyclic ring; and, in addition, only $R^1$ may be H;

$R^2$ and $R^3$ represent H or $C_1$-$C_{18}$ alkyl;

$R^6$, $R^7$, $R^8$, and $R^9$ independently represent $C_1$-$C_{24}$ alkyl, and $C_4$-$C_7$ polymethylene which are cyclizable forming a spiro cycloalkylene substituent with the C atom of the piperidine ring; and, n is an integer in the range from 2 to about 18.

2. The poly(AAMID) oligomer of claim 1 wherein said R represents one or more of the following:

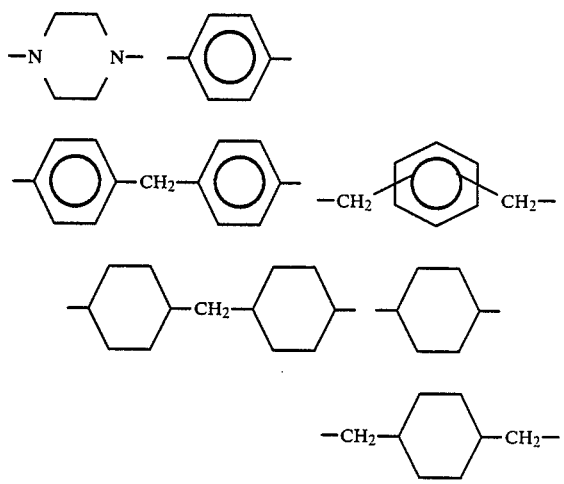

3. The poly(AAMID) oligomer of claim 2 wherein $R^4$, $R^5$, $R^6$, $R^7$, $R^8$, and $R^9$ independently represent $C_1$-$C_5$ lower alkyl.

4. The poly(AAMID) oligomer of claim 2 having a number average molecular weight in the range from about 1500 to about 20,000, and n is an integer in the range from 2 to about 10.

5. A stabilized composition of matter which comprises a UV light sensitive synthetic resinous material subject to the deleterious effects of oxygen and heat, and from about 0.01 percent to about 10 percent by weight of a poly(α-aminoacetamide) ("poly(AA-MID")) oligomer represented by the following structure:

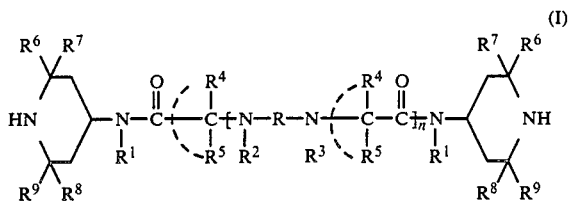

wherein, R represents $C_2$-$C_{18}$ alkylene, $C_6$-$C_{18}$ aryl, $C_7$-$C_{18}$ alkaryl or aralkyl, methylene-bis-$C_6$-$C_{18}$ aryl, piperazinediyl or aryl substituted with Cl or Br, $C_1$-$C_6$ alkoxy, monocyano, or mononitro;

$R^1$, $R^4$ and $R^5$ represent a substituent selected from the group consisting of $C_1$-$C_{20}$ alkyl, hydroxyalkyl, and N-alkylaminoalkyl, with $R^4$ and $R^5$ in combination being cyclizable to form a 5- to 8-membered alicyclic ring, typically cyclohexyl or cycloheptyl; and, in addition, only $R^1$ may be H;

$R^2$ and $R^3$ represent H or $C_1$-$C_{18}$ alkyl;

$R^6$, $R^7$, $R^8$, and $R^9$ independently represent $C_1$-$C_{24}$ alkyl, and $C_4$-$C_7$ polymethylene which are cyclizable forming a spiro cycloalkylene substituent with the carbon atom of the piperidine ring; and, n is an integer in the range from 2 to about 18.

6. The composition of claim 5 wherein said material is a polyolefin selected from the group consisting of polyethylene and polypropylene.

7. A method for preparing a poly(α-aminoacetamide) ("poly(AAMID") oligomer represented by the following structure:

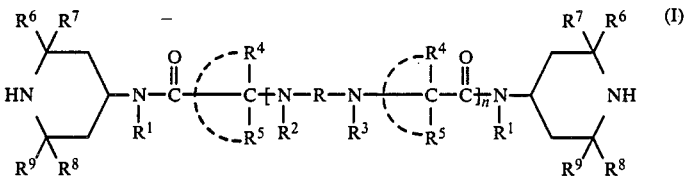

wherein, R represents $C_2$-$C_{18}$ alkylene, $C_6$-$C_{18}$ aryl, $C_7$-$C_{18}$ alkaryl or aralkyl, methylene-bis-$C_6$-$C_{18}$ aryl, piperazinediyl or aryl substituted with Cl or Br, $C_1$-$C_6$ alkoxy monocyano, or mononitro;

$R^1$, $R^4$ and $R^5$ represent a substituent selected from the group consisting of $C_1$-$C_{20}$ alkyl, hydroxyalkyl, and N-alkylaminoalkyl, with $R^4$ and $R^5$ in combination being cyclizable to form a 5- to 8-membered alicyclic ring, typically cyclohexyl or cycloheptyl; and, in addition, only $R^1$ may be H;

$R^2$ and $R^3$ represent H or $C_1$-$C_{18}$ alkyl;

$R^6$, $R^7$, $R^8$, and $R^9$ independently represent $C_1$-$C_{24}$ alkyl, and $C_4$-$C_7$ polymethylene which are cyclizable forming a spiro cycloalkylene substituent with the C atom of the piperidine ring; and, n is an integer in the range from 2 to about 18, which process comprises, (a) reacting (i) a primary diamine wherein said R is intermediate the primary amine groups, and (ii) a monoketone with a 4-alkylamino polysubstituted piperazine, in the presence of a base and sufficient haloform to provide said oligomer having the designated repeating unit, said monoketone being present in an amount from about 2 to about 25 times greater than the molar amount required to react with said diamine;

(b) maintaining the temperature during reaction below that which degrades said diamine; and, (c) recovering said oligomer having piperidyl chain ends.

8. The process of claim 7 wherein said monoketone is selected from the group consisting of acetone, 2-butanone, and cyclohexanone.

9. The process of claim 7 wherein said haloform is chloroform.

10. The process of claim 7 wherein said base is an aqueous alkali metal hydroxide.

* * * * *